United States Patent [19]

Pannell

[11] Patent Number: 5,288,632
[45] Date of Patent: Feb. 22, 1994

[54] ENCAPSULATION OF MATERIAL IN MICROBIAL CELLS

[75] Inventor: Nahida A. Pannell, Hagley, England

[73] Assignee: AD2 Limited, Birmingham, England

[21] Appl. No.: 402,347

[22] Filed: Sep. 5, 1989

Related U.S. Application Data

[63] Continuation-in-part of Ser. No. 37,182, Apr. 10, 1987, abandoned.

[30] Foreign Application Priority Data

Apr. 12, 1986 [GB] United Kingdom ............... 8608964

[51] Int. Cl.$^5$ .................. C12N 1/00; C12N 1/12; C12N 1/14; C12N 1/06
[52] U.S. Cl. ........................... 435/243; 264/4; 424/408; 426/650; 426/651; 435/252.1; 435/254.1; 435/255.1; 435/259
[58] Field of Search ............ 435/243, 253, 254, 255, 435/256, 252.1, 254.1, 255.1, 259; 426/62, 650, 651; 424/93, 408; 264/4

[56] References Cited

U.S. PATENT DOCUMENTS

| | | | |
|---|---|---|---|
| 3,681,199 | 8/1972 | Rokitansky | 435/256 |
| 4,001,480 | 1/1977 | Shank | 428/411 |
| 4,696,863 | 9/1987 | Matsushita et al. | 426/450 X |

FOREIGN PATENT DOCUMENTS

| | | |
|---|---|---|
| 0085805A | 8/1983 | European Pat. Off. |
| 0085805 | 8/1983 | European Pat. Off. |
| 0085805B | 3/1986 | European Pat. Off. |
| 2162147 | 1/1986 | United Kingdom |

Primary Examiner—David M. Naff
Attorney, Agent, or Firm—Stevens, Davis, Miller & Mosher

[57] ABSTRACT

Microbial encapsulation of materials is carried out by mixing a microbe with an encapsulatable material in liquid form in an aqueous medium to form an aqueous emulsion of the encapsulatable material. The encapsulatable material in the emulsion is absorbed into the microbe by diffusing across the microbe cell wall. The microbe has a lipid content of less than 40% by weight such as up to about 5% and may contain about 50-75% of the encapsulatable material. The emulsion is formed in the absence of a surfactant and the microbe is not treated with a lipid-extending substance or a plasmolyzer. The encapsulatable material can have a benzene or naphthalene ring and may be a perfume, an insecticide or a drug. If the material is normally solid, it can be dissolved in a solvent. The microbe may be treated to enhance permeability prior to or during encapsulation. After encapsulation, the microbe can be separated from the medium by centrifuging, freeze drying or spray-drying. Material encapsulated can be released by rupture of the microbe cell wall.

16 Claims, No Drawings

ENCAPSULATION OF MATERIAL IN MICROBIAL CELLS

This application is a continuation-in-part of application Ser. No. 07/037,182, filed Apr. 10, 1987, now abandoned.

This invention relates to microbial encapsulation, i.e. encapsulation of materials in microbial cell capsules, and to microbially encapsulated materials produced thereby.

A method of producing microbially encapsulated materials is proposed in U.S. Pat. No. 4,001,480. According to that Specification, microbes typified by fungi are cultivated to produce a very high natural fat content, i.e. microbial lipid content, of about 40 to 60% by weight, and the microbes are placed in contact with materials which are soluble in the microbial lipid so that the materials pass into the lipid and are retained passively therein.

Another method of producing microbially encapsulated materials is described in European Patent Specification No. 0085805B and United Kingdom Patent Application Publication No. 2162147A. According to Specification No. 0085805B, microbes typified by fungi which may have a microbial lipid content significantly less than 40% by weight are treated with defined organic liquid lipid-extending substances and with materials which are soluble or microdispersible in those substances so that both the lipid-extending substance and the material which is soluble or microdispersible therein enter and are retained passively with the microbe. According to Publication No. 2162147A, microbes typified by fungi, having a microbial lipid content of less than 10% by weight, are treated with an organic liquid being a lipid-extending substance as described in Specification No. 0085805B, optionally with a material dissolved or microdispersed in the organic liquid, until one or more glistening globules of the organic liquid can be observed to be retained passively in the microbe. The organic liquid lipid-extending substances employed in the method described in Specification No. 0085805B and Publication No. 2162147A are miscible with the microbial lipid and are retained passively within the microbe. Suitable substances are indicated by, for instance, being miscible with an equal quantity of soybean oil.

The aforementioned prior methods rely either on special microbe cultivation conditions to enhance the microbial lipid content to a very high level or on the use of a lipid-extending substance, and the materials to be encapsulated must be either soluble in the microbial lipid or soluble or microdispersible in the lipid-extending substance, respectively.

In French Patent Specification No. 2179528 there is described a method of causing certain materials to be absorbed and/or fixed by microbes, in which a microbe such as pressed industrial yeast is treated with a plasmolyser, i.e. a substance which causes contraction or shrinking of the microbial cytoplasm by exosmosis of cytoplasmic fluid, and then an aqueous solution of a material such as neodymium chloride, magnesium chloride or onion juice is added under certain conditions so that the aqueous material is absorbed in place of the extracted cytoplasmic fluid.

In U.S. Pat. No. 3,681,199 there is described a process for producing yeast of increased dry solid content, low plasticity and high stability by subjecting a yeast suspension to the action of specifically urea or glycerol under particularised conditions of time, filtration/centrifugation and storage. That process appears to be akin to a plasmolysing treatment of the yeast in order to remove intracellular water and thereby cause shrinkage of the yeast to produce a high solids content.

In U.S. Pat. No. 4,696,863, issued Sept. 29, 1987, there are described biocapsules of Eumycetes, particularly yeasts and preferably dead yeasts, having a lipid content of less than 10% by weight, containing a hydrophobic or hydrophilic substance or a photohardenable resin and a photopolymerisation initiator. The method of producing the biocapsules, as shown in all of the Examples in that Specification, comprises preforming the substance to be encapsulated into an aqueous emulsion using a surfactant and then adding the yeast gently to the preformed emulsion at an elevated temperature.

It is now found that, in contrast to the beliefs and principles indicated by the aforementioned proposals, it is possible to produce stable microbially encapsulated materials from microbes which do not need to have a high microbial lipid content, by a method which does not employ a lipid-extending substance or a plasmolyser, does not require pre-emulsification of the material to be encapsulated and does not require addition of a surfactant.

The present invention provides a method for the production of a microbially encapsulated material, comprising:

treating a grown intact microbe such as a fungus, bacterium or alga, having a microbial lipid content of significantly less than 40% by weight, with an encapsulatable material in liquid form which is capable of diffusing into the microbial cell without causing total lysation thereof, said treatment comprising contiguously mixing (i.e. mixing to attain contiguous contact) the microbe with the encapsulatable material liquid in the presence of an aqueous medium to produce an aqueous emulsion of the encapsulatable material liquid and to maintain the aqueous emulsion during the mixing, whereby the encapsulatable material liquid is absorbed by the microbe by diffusion across the microbial cell wall and the encapsulatable material is retained passively within the microbe, the method being performed in the absence of treatment of the microbe with a lipid-extending substance or a plasmolyser.

The microbe preferably is a fungus. Typical fungi are yeasts, for instance *Saccharomyces cerevisiae* (brewer's yeast and baker's yeast), *Kluyveromyces fragilis* (dairy yeast) and *Candida utilis*, and filamentous fungi, for instance *Aspergillus niger*, *Fusarium graminearum* and *Fusarium rocqfortiae*. The spore, mycelium and giant cell forms of filamentous fungi may be employed. A filamentous fungus from which septa have been at least partially removed by a known technique such as treatment with enzyme (chitinase, proteases, etc) may be employed if desired, Other microbes which may be employed are bacteria and algae.

The microbe is in grown form, i.e. it has been harvested from its culture medium, and is intact, i.e. not lysed. Suitably the microbe is alive, at least at the commencement of the treatment; however, a microbe which has been subjected to conditions (such as by irradiation of the microbe) to destroy its ability to propagate may be employed.

Preferably the microbe has a large cell size, for example of average diameter more than about 5 microns.

Bacteria may have a smaller normal cell size of about 1 to 2 microns but may be cultivated to attain a larger size.

It is not necessary for the microbe to have a significant lipid content. Typically the lipid content may be not more than about 5%, for instance up to 3%, by dry weight of the microbe.

The encapsulatable material should be in liquid form during the treatment. Preferably the material is a liquid (including oil) in its normal state (at room temperatures or at elevated temperatures which may be employed for the treatment), although it may be normally a solid in which case it should be dissolved or microdispersed in an organic solvent or microdispersant, particularly one which is not retained passively within the microbe and thus is not truly miscible with the microbial lipid. Examples of suitable solvents and microdispersants are the lower alcohols such as methanol, ethanol and isopropanol. The solvent or microdispersant may be removed after the encapsulation treatment, such as by spray-drying or freeze-drying.

The encapsulatable material need not be soluble in any lipid forming part of the microbe. It should not cause rupturing of the microbial cell wall and preferably is not so toxic to the microbe as to kill it before encapsulation has been achieved. Materials having a benzene or naphthalene ring appear to be particularly suitable, although non-aromatic materials also may be encapsulated. Suitable materials may be found by a simple trial of the method of the invention.

Examples of materials which may be encapsulated in accordance with the invention are benzaldehyde and essential oils used in flavours or fragrances (such as garlic, clove, mint, peppermint, lavender, cedar and eucalyptus oils), pheromones (such as *Dacus oleae*, Z-11-hexadecenal and 2-9-dodecenylacetate, insecticides (such as organophosphorus compounds, e.g. Malathion and Diazinon), leuco dyes (for instance sudan blue, sudan black and crystal violet lactone), vitamins (such as Vitamins A and C), drugs (such as menthol), detergents (such as lauryl ether sulphate), rodenticides (such as alphachloralose), nematocides (such as dichlorophen), insect-repellants (such as onion extract), herbicides, fungicides, molluscicides, insect-and plant-growth regulators, water-soluble materials such as food colourants (e.g. cochineal), and oil of wintergreen.

The treatment comprises mixing the microbe with the liquid form of the encapsulatable material in the presence of an aqueous medium such that the liquid forms an emulsion in the aqueous medium, thereby attaining good dispersion and contact of the microbe with the material. The encapsulatable material liquid may be mixed with a washed microbe or an aqueous paste or slurry of the microbe, or the encapsulatable material liquid in a small quantity of water may be mixed with dry microbe. Only a small quantity of aqueous medium may be employed.

In accordance with the invention it is found that by means of contiguously mixing the microbe with the encapsulatable material in the presence of an aqueous medium, particularly water, an aqueous emulsion is produced automatically and usually rapidly. The requisite emulsion is produced and maintained solely by the mixing operation and results in a high rate of encapsulation, seemingly by stimulating activity of microbial substances such as protein of the microbe to promote the emulsification and the diffusion of the encapsulatable material liquid through the microbial cell wall.

Examples of suitable treatment mixing operations to produce and maintain the aqueous emulsion are low-shear mixing and orbital shaking, for instance at 180 rpm.

The treatment may be performed at normal ambient temperatures but preferably the temperature is elevated, at least during the initial stage of the treatment, such as during at least the first 30 minutes, in order to expedite the treatment. A suitable elevated temperature may be in the range 35° to 60° C., for instance in the range 40° to 50° C.

The treatment may be continued until optimum encapsulation has been achieved. The encapsulation may be observed microscopically as one or more globules of the materials inside the microbial cell. This may take a few hours.

If desired, the microbes may be pretreated at an elevated temperature and/or with a proteolytic enzyme and/or with a chemical such as sodium hydroxide or a magnesium salt to enhance permeability prior to or in some cases during the encapsulation process. Such pretreatment may be carried out by incubating the microbe in water at an elevated temperature, for example 60° C., for approximately one hour. The microbe may then be mixed with the material to be encapsulated at a lower temperature (e.g. 20° to 35° C.). Materials which may be beneficially encapsulated by microbes which have undergone such pretreatment include volatile materials, e.g. pheromones (Z-11-hexadecenal).

After encapsulation, the microbial capsule may be treated to soften it in order to facilitate subsequent release of the encapsulated material, such as by treatment with a proteolytic enzyme or an alkali, or it may be treated to harden it in order to prevent premature liberation of the encapsulated material, such as by treatment with a dilute aqueous aldehyde solution.

Usually the microbe will be killed as a result of the encapsulation.

The microbial capsules of the invention may remain stable for a considerable time. Specimens have been found to have retained at least a majority of the encapsulated material after periods of more than a year.

By means of the method of the invention it is possible to encapsulate a much greater amount of encapsulatable material than is possible by means of a method employing a lipid-extending substance as a solvent or microdispersant for the material. Typically, the microbial capsules in accordance with the invention may contain about 50% to about 75% of encapsulated material based on the total weight of the microbially encapsulated material product. Moreover, the present invention enables the production of microbially encapsulated materials which are free of contamination by solvents and microdispersants. The only material in the microbial capsule which is not a natural part of the microbe is the encapsulatable material.

The microbially encapsulated material product may be separated from the residual treatment medium by centrifuging, freeze-drying or spray-drying, and may be employed in end-uses as a free-standing product or adhered to a substrate.

The encapsulated material may be released from the microbial capsules when desired by, for instance, chemical, biodegradation or mechanical rupture of the microbial cell wall, or by subjecting the capsules to an environment in which the material diffuses gradually out through the pores in the microbial cell wall.

One example of a use of this invention is in the provision of perfumed drawer liners and fragranced stationery, in which a coating of capsules containing odiferous material is adhered to one side of a sheet of paper, so that when the paper is subjected to pressure, for instance by rubbing, scratching or by a manual writing implement, the perfume is released. It is found that when encapsulated perfume provided according to the present invention is applied in the form of an aqueous suspension to the paper or the tissue, the microbial capsules adhere to the paper satisfactorily without the use of a binder or adhesive.

Another use of this invention is in the provision of encapsulated insecticides; such a product usually is more stable and may be more attractive to insects than are non-encapsulated insecticides.

A further use of capsules produced by the invention is in the provision of a product with controlled release characteristics; for example when the release of the encapsulated material is delayed or prolonged by a slow or gradual rupture of the microbial cells. This may be advantageous for the administration of drugs, pheromones and pesticides.

A further advantage of the present invention is in the provision of veterinary health products, such as encapsulated drugs, especially those encapsulated by yeasts which are digestable by the animals.

The invention is illustrated in the following Examples.

In the Examples, the brewer's yeast (*S. cerevisiae*) was obtained from Davenports Brewery, England, and the baker's yeast (*S. cerevisiae*) was obtained from The Distiller's Company (Yeast) Ltd, Scotland. Both yeasts are commercially available and have lipid contents of not more than about 3%.

In each Example, unless otherwise stated, the microbe was mixed with the encapsulatable material by means of a temperature-controlled low shear mixing vessel at about 180 rpm to maintain homogeneity and the product was harvested by centrifugation at 800 rpm for 15 minutes. The microbially encapsulated products were examined microscopically and, unless otherwise stated, the microbial cells were seen to contain one or more globules of the encapsulatable material occupying a major proportion of the cytoplasm of the cells.

In all of the Examples an aqueous emulsion of the encapsulatable material was produced and maintained in the presence of the microbe by means of the mixing operation.

EXAMPLE I

Pressed brewer's yeast was washed with distilled water and separated by centrifugation at 800 rpm for 10 minutes. Centrifuged yeast, as an aqueous paste containing 10 g (dry) of the yeast, was mixed with 10 g of lavender oil for 4 hours at 45° C. and the harvested product was applied to one side of paper using a handcoater. The quantity of capsules applied to the paper was of the order of 2-6 g.m$^{-2}$.

The coated paper was air-dried, and when rubbed or scratched a distinct odour of lavender oil was noticed. The lavender oil content of the cells was 74% by weight.

EXAMPLE II 15 g of washed baker's yeast containing 3 g (dry weight) of the yeast were mixed with 3 g of clove oil for 5 hours at 50° C. and the harvested capsules were air-dried.

When the dried capsules were crushed, a distinct odour of clove oil was noticed. The clove oil content of the cells was 60% by weight.

A comparative experiment of repeating this procedure except that 0.5 ml of 2-ethylhexyl acetate (a lipid-extending substance employed in the method of European Patent Specification No. 0085805B) was included with the clove oil, resulted in capsules having a clove oil content of 48% by weight and a 2-ethylhexyl acetate content of 10.5% by weight.

EXAMPLE III 20 g of washed brewer's yeast containing 4.4 g (dry weight) of the yeast were mixed with 3 g of cedar oil for 6 hours at 50° C. The cedar oil content of the cells was 70% by weight.

EXAMPLE IV 9.5 g of washed brewer's yeast containing 2.2 g (dry weight) of the yeast were mixed with 1.76 of mint oil for 5 hours at 45° C. and the harvested product was applied as an aqueous slurry to one side of tissue paper. The tissue was then air-dried. When the dried tissue was rubbed, a distinct aroma of mint was noticed. The mint oil content of the cells was 64% by weight.

EXAMPLE V 15 g of centrifuged brewer's yeast containing 3.3 g (dry weight) of the yeast were mixed with 2.3 g of pepermint oil for 4 hours at 40° C. and the harvested capsules were sprayed on tissue paper and air-dried.

Upon crushing the capsules the characteristic odour of peppermint oil was noticed. The peppermint oil content of the cells was 76% by weight.

EXAMPLE VI 15 g of washed brewer's yeast containing 3.3 g (dry weight) of yeast were mixed with 2.3 g of Eucalyptus oil for 4 hours at 45° C. and the resulting product was harvested by centrifugation at 800 rpm for 20 minutes. The harvested product, as an aqueous slurry, was sprayed on tissue paper and the tissue was air-dried.

When the capsules were crushed, a distinct aroma of Eucalyptus oil was noticed. The Eucalyptus oil content of the cells was 55% by weight.

EXAMPLE VII 10 g of an aqueous paste of brewer's yeast containing 2.2 g (dry weight) of the yeast were mixed with 2.2 g of *Dacus Oleae* for 6.5 hours at 45° C. and the harvested capsules were applied to one side of paper using a handcoater.

The coated paper was air-dried, and when the dried capsules were crushed the characteristic odour of pheromone was noticed. The pheromone content of the cells was 75% by weight.

EXAMPLE VIII 14.8 g of washed brewer's yeast containing 2.7 g (dry weight) of the yeast were mixed with 2.7 g of Malathion for 3 hours at 45° C.

The Malathion content of the cells was 75% by weight.

EXAMPLE IX 20 g of an aqueous slurry containing 5.0 g of sprayed dried baker's yeast were mixed with 5.0 g of a 5% (w/w) solution of sudan blue in ethanol for 3 hours at 35° C.

The harvested yeast capsules contained a large blue globule occupying the whole of the yeast cell.

EXAMPLE X 17 g of aqueous paste of brewer's yeast containing 4.1 g (dry weight) of the yeast were mixed with 3.3 g of lauryl ether sulphate for 6 hours at 45° C.

The harvested yeast capsules contained a large globule occupying the whole of the yeast cell.

EXAMPLE XI 15 g of washed brewer's yeast containing 3.5 g (dry weight) of the yeast were mixed with 2.7 g of methol crystals which had previously been dissolved in boiling water to provide a decongestant, for 5 hours at 50° C. The harvested product was applied as an aqueous slurry to one side of tissue paper and the tissue was then air-dried.

Upon rubbing the dried tissue, a strong odour of menthol was noticed.

EXAMPLE XII 16 g of washed brewer's yeast containing 3.7 g (dry weight) of the yeast were mixed with 2.9 g of a 10% (w/w) solution of alphachloralose in ethanol for 6 hours at 40° C.

The harvested capsules contained several small globules occupying the yeast cell.

EXAMPLE XIII 15 g of an aqueous slurry containing 5.0 g of sprayed dried baker's yeast were mixed with 5 g of a 10% (w/w) solution of dichlorophen in ethanol for 7 hours at 45° C.

The final product is a nematicide formulation in which the dichlorophen is released when the yeast cell has been digested.

EXAMPLE XIV 10 g of an aqueous paste containing 2.5 g of sprayed dried baker's yeast were mixed with 2 g of onion extract for 6 hours at 40° C.

The onion extract content of the cells was 62% by weight.

EXAMPLE XV 15.39 of washed brewer's yeast containing 3.46 g (dry weight) of the yeast were mixed with 3.46 g of oil of bitter almonds (benzaldehyde) for 4 hours at 25° C. and the harvested product was oven-dried. When the dried capsules were crushed, a distinct odour of bitter almonds occurred. The oil of bitter almond content of the cells was 55% by weight.

EXAMPLE XVI 35 g of washed baker's yeast containing 14 g (dry weight) of the yeast were mixed with 14 g of mustard oil for 4 hours at 40° C. and the harvested capsules were freeze-dried.

When the dried capsules were crushed or tasted, a strong odour and flavour of mustard was experienced. The mustard oil content of the cells was 52% by weight.

EXAMPLE XVII 21.8 g of washed brewer's yeast containing 4.7 g (dry weight) of the yeast were mixed with 4.7 g of a commercially available (ex. Dragoco) lemon fragrance for 5 hours at 40° C. and the harvested product was applied to paper and dried in a similar manner to that described in Example I.

When the dried paper was rubbed, a distinct odour of lemon fragrance was noticed.

EXAMPLE XVIII 21 g of washed brewer's yeast containing 4.5 g (dry weight) of the yeast were mixed with a commercially available (ex. Dragoco) apple blossom fragrance for 5 hours at 40° C. and the harvested product was freeze-dried.

When the dried product was crushed, a distinct odour of the fragrance occurred.

EXAMPLE XIX 15.9 of washed brewer's yeast containing 3.4 g (dry weight) of the yeast were mixed with 3.4 g of garlic oil for 4 hours at 40° C. and the product was harvested at 1000 rpm for 15 minutes and then freeze-dried.

When the dried capsules were crushed, a distinct odour of garlic oil was noticed. The garlic oil content of the cells was 60% by weight.

EXAMPLE XX 10 g of an aqueous slurry containing 2 g (dry weight) of baker's yeast were mixed with 2 g of 2,9-DDA (a pheromone) for 7 hours at 40° C.

The harvested capsules contained large globules of the pheromone occupying the yeast cell.

EXAMPLE XXI 19.0 g of washed brewer's yeast containing 3.8 g (dry weight) of the yeast were mixed with 3.8 g of Diazinon for 6 hours at 45° C. and the harvested product was freeze-dried.

The Diazinon content of the cells was 51% by weight.

For comparison, this procedure was repeated except that the Diazinon was employed as a 75% solution in xylene (a lipid-extending substance employed in the method of European Patent Specification No. 0085805B). The Diazinon content of the yeast capsule produced by this comparative experiment was about 38% by weight.

EXAMPLE XXII

Four samples of washed brewer's yeast were mixed with a commercial air-freshener fragrance for 1 hour at 45° C. The mixing of three of the samples was then continued at 25° C. for a further 1,2 and 4 hours respectively. Further details and the fragrance contents of the resulting yeast capsules are given below:

| Sample No. | Wet Yeast Slurry (g) | Dry Weight of Yeast (g) | Weight of Fragrance added (g) | Total Mixing Time (hr) | Fragrance Contents of the cell (by weight) |
|---|---|---|---|---|---|
| 1 | 17.9 | 4.02 | 4.02 | 1 | 57% |
| 2 | 17.8 | 4.0 | 4.0 | 2 | 57.5% |
| 3 | 17.4 | 3.9 | 3.9 | 3 | 61.0% |
| 4 | 16.7 | 3.77 | 3.77 | 5 | 68.4% |

The encapsulated globules of fragrance in Sample No. 4 were larger than those of the other Samples.

EXAMPLE XXIII 4 g of sprayed dried baker's yeast were mixed with 7.2 g of a 2.6% (w/w) solution of cochineal in water for 3 hours at 45° C. 10 g of the harvested product containing 3 g (dry weight) in water were mixed with 1 ml of formaldehyde solution at 20° C. for 2 hours, and the resultant capsules were washed with distilled water and separated by centrifugation at 1000 rpm for 15 minutes. Examination of the hardened product showed that the whole of the yeast cell was infused with the red dye.

EXAMPLE XXIV 20 g of washed brewer's yeast containing 4.6 g (dry weight) of the yeast were mixed with 3.7 g of a 2% (w/w) solution of crystal violet lactone in ethanol for 6 hours at 45° C.

Half of the harvested capsules were made into a 25% aqueous slurry containing 2.5 g (dry weight) of the product, and the slurry was mixed with 1 ml of 2N sodium hydroxide solution for one hour at 60° C. The pH of the final product was then adjusted to pH5 with 2N hydrochloric acid and the product was washed and separated by centrifuging at 1000 rpm for 15 minutes.

The NaOH-treated and untreated products were each applied as an aqueous slurry to the opposite side of clay-coated paper, and the papers were dried and tested for duplication using a standard office typewriter. The typewriter test gave much better copies from the paper coated with the NaOH-treated capsules.

EXAMPLE XXV

A culture of *Candida utilis* (NCYC) was grown in the following medium:

|  | $g \cdot l^{-1}$ |
| --- | --- |
| Glucose | 40 |
| Ammonium tartrate | 8 |
| Potassium dihydrogen orthophosphate | 5 |
| Magnesium sulphate | 0.2 |
| Sodium chloride | 0.1 |
| Calcium chloride | 0.01 |
| Yeast extract powder | 1.0 |

The culture was grown in 250 ml conical flasks, using an orbital shaker at 180 rpm and 30° C. for 62 hours. The grown yeast cells were harvested by centrifugation at 1000 rpm for 15 minutes.

A known weight of the aqueous slurry produced from the above culture, containing 2.9 g (dry weight) of microbe, was mixed with 2.9 g of a commercially available air-freshener fragrance for 4 hours at 40° C. and the product was harvested by centrifugation at 1000 rpm for 15 minutes and then freeze-dried.

When the dried capsules were crushed, a distinct odour of the fragrance was noticed.

EXAMPLE XXVI

A culture of *Aspergilluss niger* (CMI) was grown in the following medium:

|  | $g \cdot l^{-1}$ |
| --- | --- |
| Sucrose | 55 |
| Ammonium sulphate | 10.8 |
| Sodium dihydrogen orthophosphate | 1.0 |
| Yeast extract powder | 0.5 |
| Potassium chloride | 0.5 |
| Magnesium sulphate | 0.2 |
| Calcium chloride | 0.1 |

The culture was grown in 250 ml conical flasks, using an orbital shaker at 180 rpm and 30° C. for 42 hours. The fungal mycelium was harvested by filtration through a Whatman No. 1 filter paper, and was washed twice with distilled water.

16 g of the washed mycelium, as an aqueous slurry containing 1 g (dry weight), were mixed with 4 g of methyl salicylate (oil of wintergreen) for 2 hours at 40° C. The product was harvested by filtration through a Whatman No. 1 filter paper, the filtered product was washed with diethyl ether and air-dried.

When the dried mycelium was crushed, a distinct odour of the oil of wintergreen was noticed.

The product contained large globules of the oil occupying the majority of the fungal mycelial cells.

I claim:

1. Method for the production of a microbially encapsulated material, comprising:
    treating a grown intact microbe having a microbial lipid content of significantly less than 40% by weight, with an encapsulatable material in liquid form which is capable of diffusing into the microbial cell without causing total lysation thereof,
    said treatment comprising mixing the microbe with the encapsulatable material in the presence of an aqueous medium, but in the absence of added surfactant, to produce an aqueous emulsion of the encapsulatable material and to maintain the aqueous emulsion during the mixing,
    whereby the encapsulatable material is absorbed by the microbe by diffusion across the microbial cell wall and the encapsulatable material is retained passively within the microbe,
    wherein the encapsulatable material is not in aqueous emulsion form prior to said mixing of the microbe therewith, and
    the method being performed in the absence of treatment of the microbe with a lipid-extending substance or a plasmolyser.

2. Method according to claim 1 wherein the mixing is performed at an elevated temperature in the range 35° C. to 60° C., at least during the initial stage of the mixing.

3. Method according to claim 1 wherein the mixing is performed for a time until the desired optimum amount of one or more globules of the material can be observed microscopically within the microbial cell.

4. Method according to claim 3 wherein the resulting microbial capsule is harvested and then subjected to heat-treatment.

5. Method according to claim 1 wherein the resultant microbially encapsulated material is separated from the residual method ingredients by spray-drying or freeze-drying.

6. Method according to claim 1 wherein the microbe is selected from fungi, bacteria and algae.

7. Method according to claim 1 wherein the microbe is a filamentous fungus.

8. Method according to claim 1 wherein the microbe is alive at least at the commencement of the mixing.

9. Method according to claim 1 wherein the microbe is a fungus having a lipid content of up to about 5% by weight.

10. Method according to claim 1 wherein the microbe is a yeast.

11. Method according to claim 1 wherein the microbe is selected from *Saccharomyces cerevisiae, Candida utilis, Kluyveromyces fragilis, Aspergillus niger, Fusarium graminearum* and *Fusarium rocqfortiae.*

12. Method according to claim 1 wherein the microbe has an average cell diameter of greater than about 5 microns.

13. Method according to claim 1 wherein the encapsulatable material has a benzene or a naphthalene ring.

14. Method according to claim 1 wherein the encapsulatable material is selected from benzaldehyde, essential oils used in flavours or fragrances, pheromones, organophosphorus insecticidal compounds, leuco dyes, menthol, lauryl ether sulphate, alphachloralose, dichlorophen, onion extract, oil of wintergreen, and water-soluble food colourants.

15. A microbially encapsulated material when produced by the method according to claim 1.

16. Method for the production of a microbially encapsulated material, comprising:

treating a grown intact microbe having a microbial lipid content of significantly less than 40% by weight, with an encapsulatable material in liquid form which is capable of diffusing into the microbial cell without causing total lysation thereof, the liquid form of the encapsulatable material being selected from encapsulatable materials which are liquids in their normal state and solutions and microdispersions of encapsulatable materials in an organic solvent or microdispersant therefor, said treatment comprising mixing the microbe with the encapsulatable material in the presence of an aqueous medium, but in the absence of added surfactant, to produce an aqueous emulsion of the encapsulatable material and to maintain the aqueous emulsion during the mixing, whereby the encapsulatable material is absorbed by the microbe by diffusion across the microbial cell wall and the encapsulatable material is retained passively within the microbe, wherein the encapsulatable material is not in aqueous emulsion form prior to said mixing of the microbe therewith, and the method being performed in the absence of treatment of the microbe with a lipid-extending substance or a plasmolyser.

* * * * *